United States Patent [19]
Spinelli et al.

[11] Patent Number: 6,069,150
[45] Date of Patent: May 30, 2000

[54] USE OF DERIVATIVES OF TETRAHYDRO-BETA-CARBOLINES AS ANTIMETASTATIC AGENTS

[75] Inventors: Silvano Spinelli; Ernesto Menta; Hans-Willi Krell, all of Monza, Italy

[73] Assignee: F. Hoffman-La Roche AG, Basel, Switzerland

[21] Appl. No.: 09/142,058

[22] PCT Filed: Mar. 27, 1997

[86] PCT No.: PCT/EP97/01582

§ 371 Date: Nov. 12, 1998

§ 102(e) Date: Nov. 12, 1998

[87] PCT Pub. No.: WO97/37658

PCT Pub. Date: Oct. 16, 1997

[30] Foreign Application Priority Data

Apr. 4, 1996 [IT] Italy ................................ MI96A0664
Oct. 29, 1996 [IT] Italy ................................ MI96A2241

[51] Int. Cl.[7] .................................................. A01N 43/40
[52] U.S. Cl. ............................................. 514/312; 546/87
[58] Field of Search ........................... 514/322; 546/87

[56] References Cited

U.S. PATENT DOCUMENTS 4,539,407 9/1985 Stack et al. ............................. 546/87
5,010,077 4/1991 Braestrup et al. ................... 514/228.8
5,162,336 11/1992 Molino et al. ........................... 514/292

FOREIGN PATENT DOCUMENTS 3395 7/1963 France .
WO 92/0434
A1 3/1992 WIPO .

OTHER PUBLICATIONS

International Publication No. WO 92/04348 published Mar. 19, 1992.
International Publication No. WO 95/13289 published May 18, 1995.
AntiCancer Res., vol. 13, No. 6a, 1993, pp. 2301–2308, "PB–100: a potent and selective inhibitor of human BCNU resistant glioblastoma cell multiplication".
Drug Res., vol. 28, No. 1, 1978, pp. 42–46, "Major pharmacological effects of 6–methoxytetrahydro–beta carboline, a drug elevating the tissue 5–hydroxytryptamine level".

Primary Examiner—Dwayne C. Jones
Attorney, Agent, or Firm—Arent Fox Kintner Plotkin & Kahn

[57] ABSTRACT

The present invention concerns the use of beta-carboline derivatives of formula I bearing at least a free or esterified carboxylic group on the piperidine ring, for the preparation of pharmaceutical compositions having antimetastatic properties.

10 Claims, No Drawings

USE OF DERIVATIVES OF TETRAHYDRO-BETA-CARBOLINES AS ANTIMETASTATIC AGENTS

The present application is a national stage entry of International Application No. PCT/EP97/01582 filed on Mar. 27, 1997.

The present invention concerns the use of derivatives of tetrahydro-beta-carbolines for the preparation of pharmaceutical compositions having antimetastatic properties.

The metastasizing tumor cells are capable to migrate from the primary tumor toward the target organs by means of a mechanism which encompasses the penetration through the blood vessel walls, the entrance of the tumor cells into the blood f low, followed-by the successive crossing of the vessel's walls to reach the target organ.

The penetration through the connective tissue of the vessels is accomplished by the degradation of the extracellular matrix by means of the metalloproteinases released by the resident connective tissue cells, which are activated by the tumor cells. Such a mechanism, which is shared also by the not tumor tissues, is usually in a dynamic equilibrium with the connective tissue regeneration, while it is expressed in an uncontrolled way in the invading cells such as the tumor or inflammatory cells and it is involved in several pathologies such as rheumatoid arthritis, osteoarthritis, septic arthritis, cornea's ulcerations, epidermic or gastric ulceration, coronary thrombosis, proteinuria (WO 95/13289).

In such processes three types of metallo-proteinases are involved: collagenases, gelatinases and stromelysins. In normal conditions their release and their activity are strictly controlled by endogenic proteinases-inhibitors, such as for example $\alpha_2$-macroglobulin.

Therefore, metallo-proteinase inhibitors may be useful in the treatment of the pathological conditions above described as well as of the pathological consequences of traumas or also as contraceptive agents, since the metallo-proteinases are involved in the ovulation process and in the successive implant of the ovule on the uterine wall. In particular, the inhibition of the tumor metastasis by means of metalloproteinase inhibitors is described in Matrisian et al., PNAS USA, 83, 9413–7 (1986); Wilhelm et al., PNAS USA, 84, 6725–29 (1987); Werb et al., J. Cell Biol., 109, 872–89 (1989); Liotta et al., Lab. Invest., 49, 636–49 (1983).

Metallo-proteinase inhibitors are described in U.S. Pat. No. 4,511,504, U.S. Pat. No. 4,568,666, U.S. Pat. No. 4,771,037, WO 95/13289.

Beta-carboline derivatives are described to possess various pharmacological activities, such as for example antitumor activity [Anticancer Res., 13(6A), 2301–8 (1993); J. Antibiot., 46(11), 1672–7 (1993); EP 357.122], antiulcer activity [WO 92/04348 (19.03.92)], antimalarial activity [J. Nat. Prod., 54(5), 1360–7 (1991)] or are described as agents that enhance the absorption of antitumor drugs (JP 04275221).

None of such molecules is however described to have antimetastatic activity.

We have surprisingly found that the tetrahydro-betacarbolines of formula (I) are endowed with a very high activity of inhibition of the metastatic process:

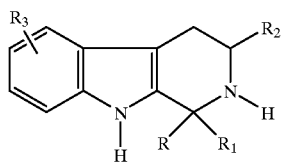

wherein:
R is selected in the group comprising hydrogen, linear or branched ($C_1$–$C_5$)alkyl, phenyl (optionally substituted with a ($C_1$–$C_5$)alkoxy group), —$(CH_2)_n$—COOH, wherein n is an integer from 1 to 3;
$R_1$ is hydrogen or a —$COOR_4$ group, wherein $R_4$ is hydrogen or ($C_1$–$C_5$)alkyl;
$R_2$ is hydrogen or a —$COOR_4$ group as above defined;
$R_3$ is selected in the group comprising hydrogen, halogen (chlorine, bromine, fluorine or iodine), ($C_1$–$C_4$)alkoxy, benzyloxy.

Object of the present invention is the use of the compounds of formula (I), as antimetastatic agents and as inhibitors of the tumor invasion process.

Also the enantiomers, the racemates and the diastereoisomers of the compounds of formula (I) are encompassed in the present invention, as well as their salts with pharmaceutically acceptable acids or bases.

Preferred examples of compounds of formula (I) are:
6-methoxy-1,2,3,4-tetrahydronorharmane;
1,2,3,4-tetrahydronorharman-3-carboxylic acid;
6-methoxy-1,2,3,4-tetrahydronorharman-1-carboxylic acid;
1-(4-methoxyphenyl)-1,2,3,4-tetrahydronorharman-3-carboxylic acid;
1-metil-1,2,3,4-tetraidronorharman-3-carboxylic acid;
1-methyl-1,2,3,4-tetrahydronorharman-1,3-dicarboxylic acid;
1-(diethylmethyl)-1,2,3,4-tetrahydronorharman-3-carboxylic acid;
(6-bromo-1,2,3,4-tetrahydronorharman-1-yl)-3-propionic acid;
1-isobutyl-1,2,3,4-tetrahydronorharman-3-carboxylic acid;
1-phenyl-1,2,3,4-tetrahydronorharman-3-carboxylic acid;
1-propyl-1,2,3,4-tetrahydronorharman-3-carboxylic acid;
1-methyl-1-methoxycarbonyl-6-benzyloxy-1,2,3,4-tetrahydronorharmane;
1-methyl-1-methoxycarbonyl-6-methoxy-1,2,3,4-tetrahydronorharmane;
1-methyl-1-methoxycarbonyl-6-hydroxy-1,2,3,4-tetrahydronorharmane;
1-methyl-1-methoxycarbonyl-6-chloro-1,2,3,4-tetrahydronorharmane;
1-methyl-1-methoxycarbonyl-6-bromo-1,2,3,4-tetrahydronorharmane;
1-methyl-1-methoxycarbonyl-1,2,3,4-tetrahydronorharmane.

The compounds encompassed in the present invention are known compounds and are commercially available or can be obtained by extraction from plants or synthesized according to methods reported in literature (see for example WO 92/04348).

The compounds of the present invention have been tested in a pharmacological "in vitro" test of inhibition of MMP8 (human neutrophil collagenase). Said test provides for the determination via fluorescence of the inhibition of the degradation of a fluorescent substrate (DNP-Pro-Leu-Gly-Leu-Trp-Ala-D-Arg-$NH_2$, M1855 Bachem) by means of the catalytic domain of MMP8.

Reagents:
1) DNP-substrate=DNP-Pro-Leu-Gly-Leu-Trp-Ala-D-Arg-NH$_2$ (M1855 Bachem), M.W. 977.1 g/mol, concentration 25 ($\mu$M in DMSO; 2) measurement buffer=50 mM TRIS/100 mM NaCl/10 mM CaCl$_2$.2H$_2$O, adjusted at pH 7.6 with hydrochloric acid. 3) Enzyme=catalytic domain of MMP8 (92 Kda), concentration 0.055 mg/ml in TRIS buffer. Substrate and enzyme are maintained at 0° C. with ice bath.

Inhibition assay:

Total volume=1 ml of solution kept under stirring in a cuvette.

Control: 0.98 ml DMSO
  0.01 ml of DNP-substrate
  0.01 ml of enzyme

Assay: 0.98 ml DMSO
  0.01 ml DNP-substrate
  0.01 ml of enzyme
  0.01 ml of inhibitor (10 (g/ml).

It is measured the fluorescence at 346 nm both of the control solution (without inhibitor) and of the solution containing the inhibitor. The inhibition of the catalytic activity of MMP8 results in the decrease in the DNP-substrate lysis, with related decrease in the fluorescence of the solution.

The percentage of inhibition is expressed by the following formula:

% Inhibition=100−(rel. unit/time$_{with\ inhibitor}$/rel. unit/time$_{control}$×100)

By repeating the experiment at different concentrations of inhibitor it is possible to determine the IC$_{50}$ value.

Table I shows the data of enzymatic inhibition for some representative compounds of the invention.

TABLE I

| compound | % Inhibition (conc. $\mu$g/ml) | IC$_{50}$ ($\mu$/ml) |
|---|---|---|
| 6-methoxy-1,2,3,4-tetrahydro-norharmane | 100 (0.1) | 0.06 |
| 1,2,3,4-tetrahydronorharman-3-carboxylic acid | 100 (0.1) | 0.07 |
| 6-methoxy-1,2,3,4-tetrahydro-norharman-1-carboxylic acid | 100 (10) | 0.05 |

The compounds of the present invention have also shown activity in an "in vivo" test of chemoinvasion. In the test of chemoinvasion the Costar Transwell chambers for cell culture (diameter: 6.5 mm; pore size: 8 $\mu$m) are coated with 100 $\mu$l of Type IV collagen (diluted solution 50 $\mu$g/ml, then evaporation overnight). With the same procedure the chambers are coated with a second layer of Type IV collagen (100 $\mu$l of solution at concentration 50 $\mu$g/ml). Before use, the chambers are rinsed twice with sterile water and incubated for about 1 hour at 37° C. in a serum-free medium (DMEM).

The human fibrosarcoma HT1080 cells are harvested by trypsin-EDTA treatment, washed with DMEM+10% FCS and incubated for at least 30 minutes at 37° C. in the same medium. The cells are then washed with serum-free DMEM and resuspended in serum-free DMEM added with 0.1% BSA (fraction V), counted and diluted to obtain a final density of 3×10$^5$ cell/ml.

Preincubated inserts are aspirated to remove the serum-free medium. The lower compartment of the chambers is filled with 600 $\mu$l of DMEM+20% FCS+1% BSA (fraction V)+compound to test. 200 $\mu$l of cell suspension (6×10$^4$ cells) containing the compound to test are added to the upper compartment and the chambers are incubated at 37° C. under humid atmosphere with CO$_2$. After first 24 hour incubation the media from both lower and upper compartments are replaced by fresh suspensions and the chambers are incubated for additional 24 hours.

Incubated filters are then washed with PBS, the cells are fixed 15 min in 4% paraformaldehyde, permeabilized in methanol (10 minutes, −20° C.) and stained with May-Grunwald-Giemsa. Cells which adhere to the top of the filters are removed with a cotton swab, filters are detached from the bottom of the chambers and analyzed with microscope to determine the number of cells on the lower side of the filters.

In a control experiment in absence of metallo-proteinase inhibitor, HT1080 cells, which overexpress metallo-proteinases, are able to degrade Type IV collagen and to migrate to the lower side of the filters. In the experiment with the inhibitor however the activity of the metallo-proteinases is partially or totally inhibited and the number of cells which migrate to the lower side of the filters is decreased. The result of the experiment is expressed by the difference between the cells counted on the lower side of the filters in the control run and in the experiment with the inhibitor.

Table II shows the data of two representative compounds of the invention.

TABLE II

| compound | chemoinvasion (conc., % inhibition) | IC$_{50}$ |
|---|---|---|
| 6-methoxy-1,2,3,4-tetrahydro-norharmane | 10$^{-6}$ M, 61.75 | 0.24 |
| 6-methoxy-1,2,3,4-tetrahydro-norharman-1-carboxylic acid | 10$^{-7}$ M, 56.5 | 0.2 |

From what it is said above it appears that the compounds of the invention may be used in the treatment of the conditions associated with the activity of the matrix metallo-proteinases, such as rheumatoid arthritis, osteoarthritis, septic arthritis, ulceration of the cornea, epidermic or gastric ulcerations, coronary thrombosis, proteinuria, pathological consequences of traumas or even as contraceptive agents.

The compounds of the present invention can be administered in doses ranging from 0.01 mg to 0.4 g per kilogram of body weight daily. A preferred dosage regimen to obtain best results is that which provides for the use from about 1 mg to about 50 mg per kilogram of body weight daily, employing unitary doses such as to administer in 24 hours from about 70 mg to about 3.5 g of the active compound to a patient having approximately 70 kg of body weight. Such a dosage regimen may be adjusted to achieve the best therapeutical effect. For example, doses may be administered taking into account the therapeutical situation of the patient. The active compound may be administered by oral, intravenous, intramuscular or subcutaneous route.

The pharmaceutical compositions of the present invention contain therapeutical effective amounts of at least one compound of the invention in admixture with pharmaceutically compatible excipients.

Oral compositions will generally include an inert diluent or an edible carrier. They can be included in gelatin capsules or compressed into tablets. Other oral administration forms are capsules, pills, elixirs, suspensions or syrups.

The tablets, pills, capsules and similar compositions can contain the following ingredients (in addition to the active compound): a binder such as microcrystalline cellulose, tragacanth or gelatin; an excipient such as starch or lactose;

a disintegrating agent such as alginic acid, primogel, maize starch and the like; a lubricant such as magnesium stearate; a fluidifier such as colloidal silicon dioxide; a sweetening agent such, as sucrose or saccharine or a flavoring agent such as mint flavor, methyl salicylate or orange flavor. When the composition selected is in form of capsules, it can contain in addition a liquid carrier such as a fat oil. Other compositions can contain various material which change the physical form thereof, for example coating agents (for tablets and pills) such as sugar or shellac. The material used in the preparation of the compositions should be pharmaceutically pure and non toxic at the used dosages.

For the preparation of pharmaceutical compositions for the parenteral administration, the active ingredient can be included in solutions or suspensions, which can comprise in addition the following components: a sterile diluent such as water for injections, saline solution, oils, polyethylene glycols, glycerin, propylene glycol or other synthetic solvents; antibacterial agents such as benzyl alcohol; antioxidants such as ascorbic acid or sodium bisulfite; chelating agents such as ethylenediaminotetracetic acid; buffers such as acetates, citrates or phosphates and agents for adjusting the tonicity of the solution, such as sodium chloride or dextrose. The parenteral preparation can be included in ampoules, mono-dose syringes, glass or plastic vials.

We claim:

1. A method for inhibiting metallo-proteinase activity, comprising administering a compound selected from the group consisting of formula (I), enantiomers, racemates, diastereoisomers, salts, and pharmaceutically acceptable acids and bases thereof, to a patient in need of such inhibition

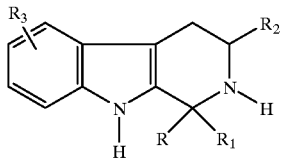

(I)

wherein:
R is selected from the group consisting of hydrogen, linear or branched ($C_1$–$C_5$) alkyl, phenyl which is unsubstituted or substituted with a ($C_1$–$C_5$) alkoxy group, and —$(CH_2)_n$—COOH, wherein n is an integer from 1 to 3;
$R_1$ is hydrogen or a —$COOR_4$ group, wherein $R_4$ is hydrogen or ($C_1$–$C_5$) alkyl;
$R_2$ is hydrogen or a —$COOR_4$ group, wherein $R_4$ is hydrogen or ($C_1$–$C_5$) alkyl;
$R_3$ is selected from the group consisting of hydrogen, halogen, ($C_1$–$C_4$) alkoxy and benzyloxy.

2. The method according to claim 1, wherein said halogen is selected from the group consisting of chlorine, bromine, fluorine and iodine.

3. The method according to claim 1, wherein said compound is selected from the group consisting of
6-methoxy-1,2,3,4-tetrahydronorharmane;
1,2,3,4-tetrahydronorharman-3-carboxylic acid;
6-methoxy-1,2,3,4-tetrahydronorharman-1-carboxylic acid;
1-(4-methoxyphenyl)-1,2,3,4-tetrahydronorharman-3-carboxylic acid;
1-metil-1,2,3,4-tetraidronorharman-3-carboxylic acid;
1-methyl-1,2,3,4-tetrahydronorharman-1,3-dicarboxylic acid;
1-(diethylmethyl)-1,2,3,4-tetrahydronorharman-3-carboxylic acid;
6-bromo-1,2,3,4-tetrahydranorharman-1-yl)-3-propionic acid;
1-isobutyl-1,2,3,4-tetrahydronorharman-3-carboxylic acid;
1-phenyl-1,2,3,4-tetrahydronorharman-3-carboxylic acid;
1-propyl-1,2,3,4-tetrahydronorharman-3-carboxylic acid;
1-methyl-1-methoxycarbonyl-6-benzyloxy-1,2,3,4-tetrahydronorharmane;
1-methyl-1-methoxycarbonyl-6-methoxy-1,2,3,4-tetrahydronorharmane;
1-methyl-1-methoxycarbonyl-6-hydroxy-1,2,3,4-tetrahydronorharmane;
1-methyl-1-methoxycarbonyl-6-chloro-1,2,3,4-tetrahydronorharmane;
1-methyl-1-methoxycarbonyl-6-bromo-1,2,3,4-tetrahydronorharmane; and
1-methyl-1-methoxycarbonyl-1,2,3,4-tetrahydronorharmane.

4. The method according to claim 3, wherein said compound is selected from the group consisting of
6-methoxy-1,2,3,4-tetrahydronorharmane;
1,2,3,4-tetrahydronorharman-3-carboxylic acid; and
6-methoxy-1,2,3,4-tetrahydronorharman-1-carboxylic acid.

5. The method according to claim 1, wherein said patient is suffering from a condition selected from the group consisting of rheumatoid arthritis, osteoarthritis, septic arthritis, ulceration of the cornea, epidermic or gastric ulcerations, coronary thrombosis, proteinuria, and pathological consequences of traumas.

6. The method according to claim 1, wherein said inhibition of metallo-proteinase activity results in the prevention of ovulation or the prevention of the implantation of an ovule on a uterine wall.

7. A method for inhibiting tumor invasion and metastases, comprising administering a compound selected from the group consisting of formula (I), enantiomers, racemates, diastereoisomers, salts, and pharmaceutically acceptable acids and bases thereof, to a patient in need of such inhibition

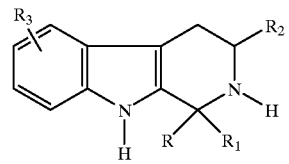

(I)

wherein:
R is selected from the group consisting of hydrogen, linear or branched ($C_1$–$C_5$) alkyl, phenyl which is unsubstituted or substituted with a ($C_1$–$C_5$) alkoxy group, and —$(CH_2)_n$—COOH, wherein n is an integer from 1 to 3;
$R_1$ is hydrogen or a —$COOR_4$ group, wherein $R_4$ is hydrogen or ($C_1$–$C_5$) alkyl;
$R_2$ is hydrogen or a —$COOR_4$ group, wherein $R_4$ is hydrogen or ($C_1$–$C_5$) alkyl;

R₃ is selected from the group consisting of hydrogen, halogen, (C₁–C₄) alkoxy and benzyloxy.

8. The method according to claim 7, wherein said halogen is selected from the group consisting of chlorine, bromine, fluorine and iodine.

9. The method according to claim 7, wherein said compound is selected from the group consisting of
   6-methoxy-1,2,3,4-tetrahydronorharmane;
   1,2,3,4-tetrahydronorharman-3-carboxylic acid;
   6-methoxy-1,2,3,4-tetrahydronorharman-1-carboxylic acid;
   1-(4-methoxyphenyl)-1,2,3,4-tetrahydronorharman-3-carboxylic acid;
   1-metil-1,2,3,4-tetraidronorharman-3-carboxylic acid;
   1-methyl-1,2,3,4-tetrahydronorharman-1,3-dicarboxylic acid;
   1-(diethylmethyl)-1,2,3,4-tetrahydronorharman-3-carboxylic acid;
   (6-bromo-1,2,3,4-tetrahydronorharman-1-yl)-3-propionic acid;
   1-isobutyl-1,2,3,4-tetrahydronorharman-3-carboxylic acid;
   1-phenyl-1,2,3,4-tetrahydronorharman-3-carboxylic acid;
   1-propyl-1,2,3,4-tetrahydronorharman-3-carboxylic acid;
   1-methyl-1-methoxycarbonyl-6-benzyloxy-1,2,3,4-tetrahydronorharmane;
   1-methyl-1-methoxycarbonyl-6-methoxy-1,2,3,4-tetrahydronorharmane;
   1-methyl-1-methoxycarbonyl-6-hydroxy-1,2,3,4-tetrahydronorharmane;
   1-methyl-1-methoxycarbonyl-6-chloro-1,2,3,4-tetrahydronorharmane;
   1-methyl-1-methoxycarbonyl-6-bromo-1,2,3,4-tetrahydronorharmane; and
   1-methyl-1-methoxycarbonyl-1,2,3,4-tetrahydronorharmane.

10. The method according to claim 9, wherein said compound is selected from the group consisting of
   6-methoxy-1,2,3,4-tetrahydronorharmane;
   1,2,3,4-tetrahydronorharinan-3-carboxylic acid; and
   6-methoxy-1,2,3,4-tetrahydronorharman-1-carboxylic acid.

* * * * *